United States Patent [19]
Zhou et al.

[11] Patent Number: 6,124,442
[45] Date of Patent: Sep. 26, 2000

[54] PROCESS FOR EXTRACTING TRITERPENE GLYCOSIDES FROM BOTANICAL SOURCES

[76] Inventors: James H. Zhou, 32 Hallmark Hill Dr., Wallingford, Conn. 06492; Weiping He, Mail Box 215, Guanxi Teacher University, Shan Li Dian, Yu Chia Rd, Guilin City, Guanzi 541004, China

[21] Appl. No.: 09/275,339

[22] Filed: Mar. 24, 1999

[51] Int. Cl.$^7$ .......................... C07H 15/00; C07H 15/24; C12N 5/00; C12N 5/02; A23L 1/22
[52] U.S. Cl. ......................... 536/4.1; 536/6.1; 435/410; 426/534
[58] Field of Search .................. 424/195.1, 93.7; 536/4.1, 6.1; 435/410, FOR 100; 426/534

[56] References Cited

U.S. PATENT DOCUMENTS

| | | | |
|---|---|---|---|
| 4,084,010 | 4/1978 | Takemoto et al. | 426/548 |
| 5,023,330 | 6/1991 | Gander et al. | 536/124 |
| 5,646,178 | 7/1997 | Walker et al. | 514/456 |

FOREIGN PATENT DOCUMENTS 1019935  1/1993  China.

*Primary Examiner*—David M. Naff
*Assistant Examiner*—Deborah K. Ware
*Attorney, Agent, or Firm*—Bachman & LaPointe, P.C.

[57] ABSTRACT

The process includes obtaining a liquid extract from a fresh plant source material and mixing the extract with a solution saturated with at least one element having an oxidation number of one or two or combinations thereof. The resulting mixture provides for a solid precipitate material and a liquid portion containing the triterpene glycosides of which is then passed through a macroporous resin. The resin is then washed with an alcohol to obtain a solution thereof containing the triterpene glycosides. The solution is condensed to provide a purified liquid triterpene glycoside solution and then a drying step is performed to obtain a dry composition containing the triterpene glycosides.

27 Claims, 1 Drawing Sheet

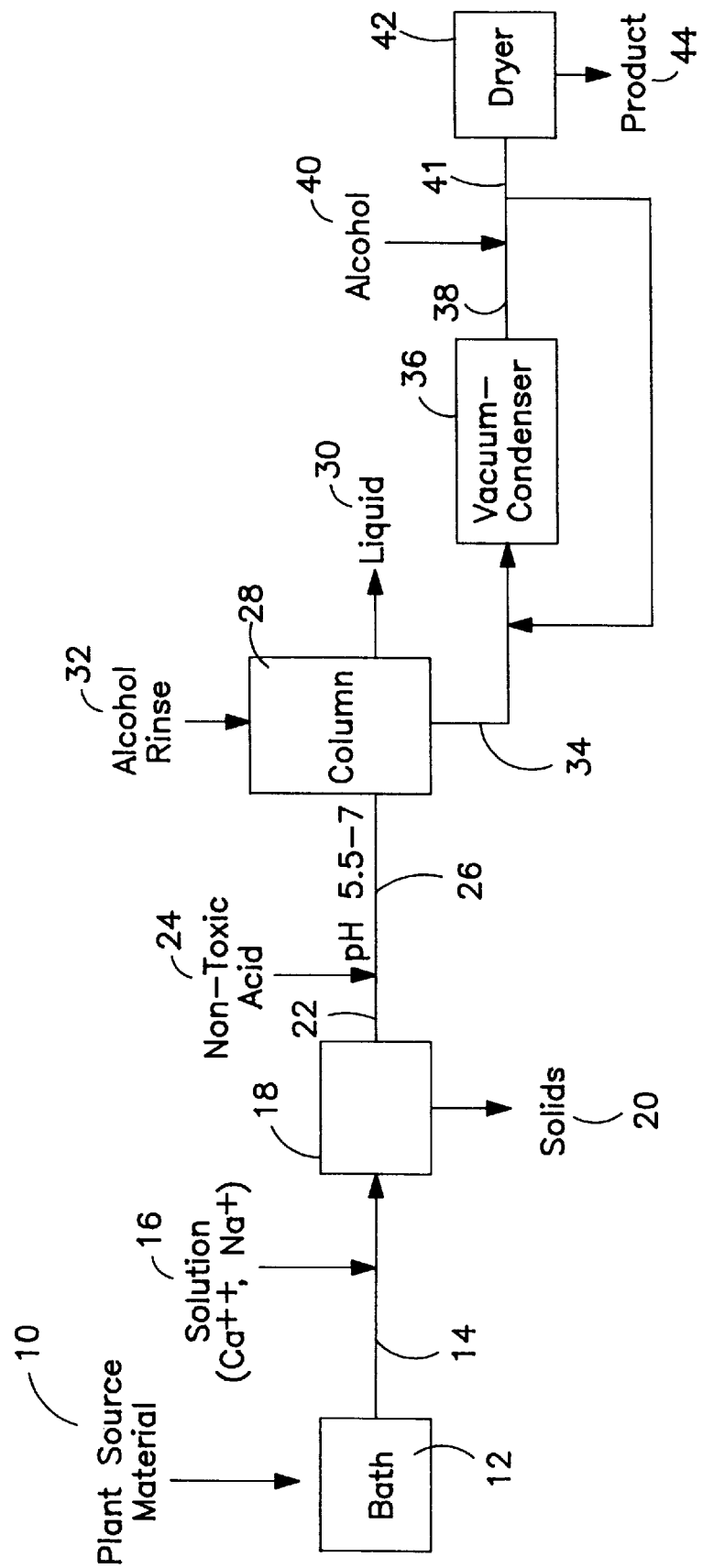

PROCESS FOR EXTRACTING TRITERPENE GLYCOSIDES FROM BOTANICAL SOURCES

BACKGROUND OF THE INVENTION

The invention relates to a process for extracting triterpene glycosides from plant or botanical sources.

Triterpene glycosides are non-caloric and are intensely sweet. For this reason, triterpene glycosides are very attractive for use as a sweetening agent in dietary and food industries.

Plant or botanical sources exist for obtaining triterpene glycosides such as mogroside V. One particularly good sources of triterpene glycoside is cucurbitaceae fruit, fructus mormordicae or momordica grosvenori, which is also widely known as Lo Han Kuo. This plant itself is widely and popularly consumed as a food for a wide variety of health purposes such as stomach distress, sore throat, cough, diarrhea, constipation, etc. However, this fruit also contains bitter tasting compounds, which to date are not specifically identified to the knowledge of the present inventors, which interfere with use of the fruit or simple extract of the fruit as a sweetening agent.

One laboratory extraction process was developed and published by Tsunematsu Takemoto et al. The Takemoto et al. process, however, is only applicable to roasted dry material from the fruit. In addition, the Takemoto et al. process is rather complicated, provides low yield, and is not practical or economical on an industrial scale.

Another disclosed process is set forth in CN 1019935. In this process, fruit juice is obtained directly from momordica grosvenori, with no provision for removal of bitter-tasting materials. Thus, the process disclosed in CN 1019935 can only produce crude triterpene glycoside-containing material which also contains bitter components and which is not suitable for industrial scale manufacture or use as a sweetener.

It is therefore the primary object of the present invention to provide a process whereby triterpene glycosides can be extracted from plant or botanical sources such as momordica grosvenori with a very high yield, and without including bitter-tasting components in the final product.

It is a further object of the present invention to provide such process which is simple, efficient, consistent and economic.

It is a still further object of the present invention to provide such a process which can be carried out using fresh fruit, thereby completely avoiding the need for fruit drying processes.

It is another object of the present invention to provide such a process which does not involve the use of excessive amounts of organic or inorganic chemicals and the like.

Other objects and advantages of the present invention will appear hereinbelow.

SUMMARY OF THE INVENTION

In accordance with the present invention, the foregoing objects and advantages have been readily attained.

According to the invention, a process is provided for obtaining triterpene glycosides from a plant source, which process comprises the steps of providing a plant source material containing triterpene glycosides, obtaining a liquid extract from said source material, said liquid extract containing said triterpene glycosides; mixing said liquid extract with a solution saturated with at least one element selected from the group consisting of elements having an oxidation number of two, elements having an oxidation number of one, and combinations thereof so as to provide a mixture; allowing said mixture to rest so as to provide a solid precipitate material and a liquid portion containing soluble portions of said liquid extract including said triterpene glycosides; passing said liquid portion through a column containing a neutral absorptive macroporous resin so as to absorb portions of said liquid portion including said triterpene glycosides onto said neutral absorptive macroporous resin; rinsing said column with an alcohol so as to obtain an alcohol solution containing said triterpene glycosides; condensing said alcohol solution so as to provide purified liquid triterpene glycoside solution; and drying said purified liquid triterpene glycoside solution so as to provide a dry composition containing said triterpene glycosides.

The process is particularly advantageous when used with momordica grosvenori. The process provides an end product which is substantially free of bitter-tasting components and which contains a very high yield of the desired triterpene glycosides. The process is ideal for industrial scale use, and the end product is substantially free of insoluble components.

BRIEF DESCRIPTION OF DRAWING

A detailed description of preferred embodiments of the present invention follows, with reference to the attached FIGURE, which schematically illustrates a process in accordance with the present invention.

DETAILED DESCRIPTION

The invention relates to a process for extracting triterpene glycosides from plant or botanical sources. The process advantageously provides for extraction of triterpene glycosides and separation of bitter-tasting components normally present in the plant source material. In addition, the process is simple, efficient and economical and is therefore ideally suited for use in manufacture on an industrial scale of triterpene glycosides which are extremely useful in the manufacture of non-caloric or low calorie sweeteners and a wide variety of food products.

The invention is particularly well suited for use in extracting triterpene glycosides from plant members of the cucurbitaceae family (fructus mormordicae or momordica grosvenori) which is also widely known in Chinese as Lo Han Kuo. The following description of preferred embodiments of the invention will be presented in terms of momordica grosvenori. It should of course be noted, however, that other plant or botanical sources of triterpene glycosides could be used within the broad scope of the invention.

Referring to the attached FIGURE, a schematic illustration of one embodiment of the process of the present invention is provided.

The starting plant source material can advantageously be fresh plant matter, for example cut pieces of freshly harvested momordica grosvenori. The present invention provides excellent yield of triterpene glycoside, and 100 g of starting plant material can yield 1 g of highly pure triterpene glycoside.

The fresh plant pieces are extracted by soaking in a bath of heated water, alcohol (preferably ethanol) or both. The initial extraction process is preferably carried out in hot, preferably boiling water. The FIGURE shows plant source material 10 being added to extraction bath 12, and a liquid extract exiting bath 12 which contains extracted triterpene glycosides as desired, and which also typically will include bitter-tasting components from plant source material 10.

Extraction in bath 12 is preferably carried out several times for the initial starting material, each time saving the resulting liquid. For example, plant source material 10 can be boiled in a 1000 milliliter volume of extraction liquid, typically for a period of 1–3 hours. The resulting extract liquid is then preferably filtered through a suitable filter such as a 40 mesh stainless steel screen. The thus-obtained solid material can then be extracted again, for example this time using 800 milliliters of boiling water, followed by filtering and two additional extractions each using 600 milliliters of boiling water. By collecting the liquid from filtering after each extraction, a total volume of about 3000 milliliters of liquid extract containing the desired triterpene glycosides is provided. Of course, it may be preferable for a particular process to carry out more or less extraction steps, and different volumes of liquid could of course be used for each boiling or extraction step.

Returning to the FIGURE, liquid extract 14 is then preferably mixed with saturated solution 16 which preferably contains one or more element having an oxidation number of one or two. The saturated solution is preferably a saturated solution of calcium (Ca++), sodium (Na+) potassium (K+) and mixtures thereof. Better results are provided if the saturated solution includes at least calcium, and it is most preferred that the saturated solution contain both calcium and sodium.

For the preferred saturated solution including both calcium and sodium, it is further preferred that the saturated solution be provided having a ratio by volume of calcium saturated solution to sodium saturated solution of between about 1:1 and about 25:1, preferably between about 1:1 and about 5:1, and ideally about 3:1.

Liquid extract 14 and saturated solution 16 are mixed thoroughly and introduced to a settling tank 18 where the mixture is allowed to precipitate, preferably for a period of at least about one-half hour, and more preferably for a period of at least about three hours. Solid precipitate material 20 resulting from this step is removed from tank 18 and disposed of as desired, while the clarified liquid portion 22 is removed from tank 18 and contains triterpene glycoside for further processing in accordance with the present invention.

Liquid portion 22 exiting settling tank 18 may have a basic or alkaline pH, which is not desirable in connection with the further processing steps of the present invention. Thus, it may be necessary to mix liquid portion 22 with a non-toxic acid or acidic source 24, preferably in proportions suitable for providing the resulting mixture 26 with a pH of between about 5.5 and about 7.

Non-toxic acid 24 may suitably be any non-toxic acid which can be used to adjust the pH as desired. Examples of suitable acid include acetic acid, citric acid, HCl, $H_2SO_4$ and the like. Acetic acid is particularly preferred because it is readily available and commonly acceptable for use in food products. This step is advantageous and desirable since the precipitating step using saturated solution of Ca++, Na+ and/or K+ results in a solution having a pH greater than 7 which is undesirable and would interfere with proper operation of the process of the present invention.

In further accordance with the present invention, neutralized mixture 26 is then preferably passed to an absorptive affinity chromatography column 28 preferably containing a neutral macroporous resin. During treatment in column 28, the desired triterpene glycosides are absorbed onto the resin in column 28, and a resulting liquid product 30 exiting column 28 is disposed of as desired. After liquid 30 is removed from column 28, column 28 is then preferably rinsed using an alcohol solution 32 so as to remove absorbed triterpene glycosides from the resin in column 28 and provide a triterpene glycoside-containing alcohol solution 34 exiting column 28. Triterpene glycoside-containing alcohol solution 34 is then further treated in accordance with the process of the present invention as described below.

Rinsing with alcohol solution 32 is preferably carried out using ethanol as the alcohol rinse. Further, it has been found in accordance with the present invention that a higher yield of rinsed triterpene glycosides is obtained if the alcohol rinsing is carried out in a plurality of steps or stages, and it is further preferred that the initial alcohol rinsing step or stage be carried out using an alcohol solution having a relatively low alcohol concentration, and that a gradually increasing alcohol concentration be used for each stage until the final stage having a relatively high alcohol concentration. For example, alcohol solutions may be used having an initial alcohol concentration of about 10 percent by volume, and are preferably gradually increased to a final alcohol concentration of about 95 percent by volume. Depending upon the number of rinsing steps to be used, it is preferable that the initial rinsing step be carried out using an alcohol solution having an alcohol concentration of less than or equal to about 70 percent by volume, and further that the final rinsing stage be carried out using an alcohol solution having a final alcohol concentration of at least about 95 percent by volume.

In connection with the resin contained in column 28, any suitable neutral macroporous resin can be used. It is preferred that the resin have a surface area of between about 100 $m^2/g$ and about 1000 $m^2/g$. Such resin is commercially available.

Referring back to the FIGURE, triterpene glycoside-containing alcohol solution 34 is then preferably passed to a vacuum condenser 36 for condensing the initial volume of solution 34 to a reduced or condensed or concentrate volume 38 exiting condenser 36 which contains the desired triterpene glycosides. Condensed solution 38 is then preferably mixed with an additional volume 40 of alcohol to provide a concentrate-alcohol mixture which is preferably allowed to set so as to form a precipitate which is removed, and the remaining mixture is passed to drier 42 for a spray-drying step, preferably at a temperature of between about 50° C. and about 150° C., so as to provide a dry powder product which advantageously contains at least about 40% (wt) of triterpene glycosides, preferably at least about 60% triterpene glycosides, and most preferably at least about 80% triterpene glycosides. Further advantageously, the balance of the powder product is other carbohydrates and remaining plant matter, and is substantially free of the bitter-tasting components present in the earlier extract portions of the original plant source material. Thus, product 44 is ideally suited for use as an ingredient in various food products or in the manufacture of non-caloric sweeteners.

Product 44 is also substantially free of water insoluble materials to allow for full dissolution of product 44 in liquid products as desired.

Referring back to the FIGURE, it may be desirable to recycle the mixture 41 of alcohol 40 and condensed liquid 38 for one or more additional condensing steps. This can assist in elevating the content of triterpene glycosides in the final product.

It is also preferred that condensation be carried out in vacuum-condenser 36 so as to reduce the volume of triterpene glycoside-containing solution, preferably to a reduced volume of about 1/20 of the original incoming liquid volume. Further, alcohol 40 is preferably added in the form of a 95% ethanol alcohol solution. Alcohol 40 is preferably mixed with the 1/20 condensed solution or reduced volume in a total volume having a ratio by volume of alcohol solution to condensed solution of between about 1:1 and about 25:1, preferably between about 1:1 and about 10:1 and ideally about 5:1. It is also preferred that the additional alcohol solution 40 be added in separate discrete doses or dilutions, for example in separate doses each having substantially the same volume as the original 1/20 condensed solution. Thus, if the total alcohol solution to condensed solution ratio is 5:1, five equal doses of alcohol solution would preferably be used.

It should be noted that one advantage in accordance with the present invention is that a large portion of the sticky, insoluble materials which normally accompany momordica grosvenori is eliminated before feed to the resin in column 28. This advantageously results in less difficulty due to gumming or fouling of the resin, and further leads to high yield and high purity of the product. As set forth above, the process of the present invention advantageously provides for a very high percentage of total triterpene glycoside in the final product, as well as a large percentage advantageously in the form of mogroside V, which is an excellent indicator of the total content of triterpene glycosides in the final product. For example, a 35% (wt) mogroside V content is indicative of a minimum 80% (wt) triterpene glycoside content, and the mogroside V content is easily measured to provide for quality control and the like in an industrial scale process.

The dry composition of the process of the present invention is advantageously at least about 40 times sweeter per unit weight than refined sugar.

Although the exact bitter-tasting components contained in the original plant source material 10 are not known to the inventors at this time, the process of the present invention does advantageously remove such bitter-tasting components and therefore advantageously provides the desired high yield and high quality triterpene glycoside in a process which is simple and efficient and therefore well suited to industrial scale use.

EXAMPLE

In this example, 100 grams of fresh Cucurbitaceae fruit was cut into pieces and boiled in 1000 ml of boiling water for 3 hours. The extract was filtered through a 40 mesh stainless steel screen to remove solids, and the liquid set aside. The separated solid was then extracted again using 800 ml of water and then twice using 600 ml each to provide a total liquid extract of 3000 ml. To the 3000 ml was added 150 ml of Ca++ saturated solution and 50 ml of Na+ saturated solution, and the resulting mixture was mixed thoroughly and then set to precipitate. After about 0.5 hours, a solid had precipitated, and the clarified liquid carrying triterpene glycosides was separated from the settling tank. The liquid was mixed with acetic acid until it had a basic pH between 5.5 and 7, and the neutralized solution was then passed through an absorptive affinity chromatography column filled with 500 grams of neutral macroporous resin having a surface area of about 100–1000 $m^2/g$. The resin was then washed using 1500 ml of E—OH (ethanol) gradually increasing from a 10% vol concentration in the initial rinse to a 95% vol concentration in the final rinse. The collected liquid from the rinsing was then condensed to 1/20 of original volume using a vacuum condenser, and the condensed solution was then mixed with 5 separate volumes of 95% E—OH each equal to the volume of the original 1/20 condensed solution, and the mixture was set to precipitate E—OH insoluble materials. The clarified liquids were then filtered and vacuum-spray dried at 120° C. to form approximately 1 gram of light yellow powder which was approximately 80% triterpene glycoside, and which was entirely free of bitter tasting components.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

We claim:

1. A process for obtaining triterpene glycosides from a plant source containing triterpene glycosides, comprising the steps of:
    providing a fresh plant source material containing triterpene glycosides;
    obtaining a liquid extract from said source material, said liquid extract containing said triterpene glycosides;
    mixing said liquid extract with a solution saturated with at least one element selected from the group consisting of elements having an oxidation number of two, elements having an oxidation number of one, and combinations thereof so as to provide a mixture;
    allowing said mixture to rest so as to provide a solid precipitate material and a liquid portion containing soluble portions of said liquid extract including said triterpene glycosides;
    passing said liquid portion through a column containing a neutral macroporous resin so as to absorb portions of said liquid portion including said triterpene glycosides onto said neutral macroporous resin;
    rinsing said column with an alcohol so as to obtain an alcohol solution containing said triterpene glycosides;
    condensing said alcohol solution so as to provide a purified liquid triterpene glycoside solution; and
    drying said purified liquid triterpene glycoside solution so as to provide a dry composition containing said triterpene glycosides.

2. A process according to claim 1, wherein said source material comprises *Momordica grosvenori*.

3. A process according to claim 1, wherein said fresh plant source material further contains an initial amount of bitter-tasting components, and wherein said dry composition contains a reduced amount of bitter-tasting components.

4. A process according to claim 1, further comprising the steps of adjusting pH of said liquid portion to between about 5.5 and about 7 before passing said liquid portion to said column.

5. A process according to claim 4, wherein said adjusting step comprises mixing said liquid portion with a non-toxic acidic material.

6. A process according to claim 1, wherein said condensing step comprises condensing said alcohol solution to a reduced volume containing said triterpene glycosides to provide a concentrate, mixing said concentrate with an additional amount of alcohol to provide a concentrate-alcohol mixture, and precipitating alcohol insoluble materials so as to provide said purified liquid triterpene glycoside solution.

7. A process according to claim 6, wherein said additional amount of alcohol is an additional alcohol solution.

8. A process according to claim 7, wherein said additional alcohol solution is a 95% ethanol solution.

9. A process according to claim 7, wherein said concentrate-alcohol mixture has a ratio by volume of said additional alcohol solution to said concentrate of between about 1:1 and about 25:1.

10. A process according to claim 7, wherein said concentrate-alcohol mixture has a ratio by volume of said additional alcohol solution to said concentrate of between about 1:1 and about 10:1.

11. A process according to claim 7, wherein said additional alcohol solution is mixed with said concentrate in doses each substantially equal in volume to said concentrate.

12. A process according to claim 1, wherein said step of obtaining said liquid extract comprises boiling said source material in a bath selected from the group consisting of water, alcohol and mixtures thereof so as to provide said liquid extract.

13. A process according to claim 1, wherein said mixing step comprises mixing said liquid extract with a saturated solution of an element selected from the group consisting of calcium, sodium, potassium and mixtures thereof.

14. A process according to claim 13, wherein said saturated solution includes calcium and a second element selected from the group consisting of sodium, potassium and mixtures thereof.

15. A process according to claim 13, wherein said saturated solution includes calcium and sodium.

16. A process according to claim 15, wherein said saturated solution contains a ratio by volume of calcium saturated solution to sodium saturated solution of between about 1:1 and about 25:1.

17. A process according to claim 15, wherein said saturated solution contains a ratio by volume of calcium saturated solution to sodium saturated solution of between about 1:1 and about 5:1.

18. A process according to claim 1, wherein said column is an absorptive affinity chromatography column.

19. A process according to claim 1, wherein said rinsing step comprises rinsing said column with an ethanol solution.

20. A process according to claim 19, wherein said rinsing step comprises a plurality of rinsing steps starting with an initial ethanol solution having an initial ethanol concentration and finishing with a final ethanol solution having a final ethanol concentration greater than said initial ethanol concentration.

21. A process according to claim 20, wherein said initial ethanol concentration is less than or equal to about 70% (vol) and said final ethanol concentration is greater than or equal to about 95% (vol).

22. A process according to claim 1, wherein said drying step is carried out in a spray drier at a temperature of between about 50° C. and about 150° C.

23. A process according to claim 1, wherein said dry composition contains at least about 40% (wt) of said triterpene glycosides.

24. A process according to claim 1, wherein said dry composition contains at least about 60% (wt) of said triterpene glycosides.

25. A process according to claim 1, wherein said dry composition contains at least about 80% (wt) of said triterpene glycosides.

26. A process according to claim 1, wherein said dry composition contains at least about 35% (wt) mogroside V.

27. A process according to claim 1, wherein said neutral macroporous resin has a surface area of between about 100 $m^2/g$ and about 1,000 $m^2/g$.

* * * * *

UNITED STATES PATENT AND TRADEMARK OFFICE
CERTIFICATE OF CORRECTION

PATENT NO. : 5,124,442
DATED : September 26, 2000
INVENTOR(S) : James H. Zhou, et al.

It is certified that error appears in the above-identified patent and that said Letters Patent is hereby corrected as shown below:

In Column 1, Line 15, delete "LO" and insert --LOU-- in its place.

In Column 2, Line 45, delete "LO" and insert --LOU-- in its place.

Signed and Sealed this

Eighth Day of May, 2001

*Attest:*

NICHOLAS P. GODICI

*Attesting Officer*    *Acting Director of the United States Patent and Trademark Office*

UNITED STATES PATENT AND TRADEMARK OFFICE
CERTIFICATE OF CORRECTION

PATENT NO. : 6,124,442
DATED : September 26, 2000
INVENTOR(S) : James H. Zhou, et al.

It is certified that error appears in the above-identified patent and that said Letters Patent is hereby corrected as shown below:

Column 1,
Line 16, delete "LO" and insert -- LOU -- in its place.

Column 2,
Line 46, delete "LO" and insert -- LOU -- in its place.

Signed and Sealed this

Ninth Day of October, 2001

Attest:

NICHOLAS P. GODICI
Attesting Officer
Acting Director of the United States Patent and Trademark Office